(12) United States Patent
Nilsson

(10) Patent No.: US 9,561,252 B2
(45) Date of Patent: *Feb. 7, 2017

(54) MATERIAL FOR SEPARATION OF A BIOMOLECULE

(71) Applicant: GLYCOREX TRANSPLANTATION AB, Lund (SE)

(72) Inventor: Kurt G. I. Nilsson, Lund (SE)

(73) Assignee: GLYCOREX TRANSPLANTATION AB, Lund (SE)

( * ) Notice: Subject to any disclaimer, the term of this patent is extended or adjusted under 35 U.S.C. 154(b) by 64 days.

This patent is subject to a terminal disclaimer.

(21) Appl. No.: 14/181,097

(22) Filed: Feb. 14, 2014

(65) Prior Publication Data

US 2014/0183130 A1    Jul. 3, 2014

Related U.S. Application Data

(63) Continuation of application No. 12/597,192, filed as application No. PCT/SE2008/000309 on May 5, 2008, now Pat. No. 8,691,544.

(30) Foreign Application Priority Data

May 4, 2007 (SE) ..................... 0701141
Oct. 26, 2007 (SE) ..................... 0702431

(51) Int. Cl.

| | | |
|---|---|---|
| *A61M 1/36* | (2006.01) | |
| *A61K 35/16* | (2015.01) | |
| *B01D 15/38* | (2006.01) | |
| *B01J 20/32* | (2006.01) | |
| *G01N 37/00* | (2006.01) | |
| *B01J 20/28* | (2006.01) | |
| *B01J 20/26* | (2006.01) | |

(52) U.S. Cl.
CPC ........... *A61K 35/16* (2013.01); *B01D 15/3804* (2013.01); *B01J 20/262* (2013.01); *B01J 20/267* (2013.01); *B01J 20/28009* (2013.01); *B01J 20/3212* (2013.01); *B01J 20/3217* (2013.01); *B01J 20/3219* (2013.01); *B01J 20/3251* (2013.01); *B01J 20/3253* (2013.01); *B01J 20/3255* (2013.01); *B01J 20/3274* (2013.01); *A61M 1/3687* (2013.01); *B01J 2220/58* (2013.01); *G01N 2400/38* (2013.01)

(58) Field of Classification Search
None
See application file for complete search history.

(56) References Cited

U.S. PATENT DOCUMENTS

| 4,330,619 | A | 5/1982 | Goldstien |
| 5,372,937 | A | 12/1994 | Nilsson |
| 7,014,049 | B2 | 3/2006 | Nilsson |
| 2002/0146814 | A1 | 10/2002 | Nilsson |
| 2004/0242857 | A1* | 12/2004 | Nilsson ................ B01D 15/00 536/3 |
| 2005/0119464 | A1* | 6/2005 | Von Pawel-Rammingen .... C12N 9/641530/395 |
| 2010/0135981 | A1 | 6/2010 | Bjorck et al. |

FOREIGN PATENT DOCUMENTS

| CA | 1229808 | 12/1987 |
| WO | 03027245 | 4/2003 |
| WO | 2006131347 | 12/2006 |

OTHER PUBLICATIONS

Brenda Enzyme information System "Information on EC 3.2.1.49—alpha-N-acetylgalactosaminidase" pp. 1-20, Jan. 2, 2016.*
International Search Report mailed Sep. 4, 2008 in PCT/SE2008/000309.
International Preliminary Report on Patentability mailed Jul. 10, 2009 in PCT/SE2008/000309.
Supplementary European Search Report received in EP 08753935, mailed Sep. 7, 2011.
Schram, A. W. et al. (1978) "Properties of Immobilized Fig Alpha-Galactosidase and Effect of Ceramide-3 Content of Plasma from Patients with Fabry's Disease" Biochimica et Biophysica Acta, 527:456-464.
Bakunina, I.Y. et al. (2006) "Immobilized of Alpha-Galactosidase Inside Hybrid Silica Nanocomposites Containing Polysaccharides" Russian Journal of Applied Chemistry, 79(5):827-832.
Collin, M. et al. (2001) "EndoS, a Novel Secreted Protein from *Streptococcus pyogenes* with Endoglycosidase Activity on Human IgG" The Embo Journal, 20(12):3046-3055.
von Pawel-Rammingen, U. et al. (2002) "IdeS, a Novel Streptococcal Cysteine Proteinase with Unique Specificity for Immunoglobulin G" The Embo Journal, 21(7):1607-1615.

* cited by examiner

*Primary Examiner* — Sharon Wen
*Assistant Examiner* — James Rogers
(74) *Attorney, Agent, or Firm* — Smith, Gambrell & Russell, LLP

(57) ABSTRACT

A Product is described and which contains at least one type of ligand bound to a separation material and which allows selective binding or cleavage of a biomolecule for example in human blood.

20 Claims, No Drawings

MATERIAL FOR SEPARATION OF A BIOMOLECULE

A product material and examples of its applications are described below.

The product material involves a material containing a so-called matrix, to which a ligand has been bound. The ligand has the ability to bind selectively, (below also named 'specifically'), to another biomolecule. Non-limiting examples of ligand are a saccharide which has been bound to matrix directly or via a spacer, or to which an amino acid, glycosylated amino acid, peptide, protein, glycopeptide, glycoprotein, mucin, enzyme, antibody, mucin, lipid, glycolipid has been bound directly or via a spacer, or to which a combination of two or more of these ligands have been bound.

The product material is used alone or as a part of a product e.g. a column, a filter or as a part of for example a blood bag system used for collection of donor blood. This combined product results in the binding of biomolecules, cells, bacteria or virus to the product material.

The product may be used e.g. for reduction of proteins or of blood proteins e.g. antibodies or other specific proteins or components from whole blood or from blood plasma. When the product is binding antibodies or proteins the combined product results in e.g. a blood or a blood plasma which contains a reduced amount of specific proteins or antibodies. When used for binding of blood group antibodies, the product material results in a blood or blood plasma, below called a universal plasma, which is similar to existing AB-plasma which may be given to patients of any blood group.

The invention also relates to a combined product where the product is used in combination for example with soluble enzyme or immobilised enzyme containing product specific for cleavage of for example IgG or IgM or for cleavage of for example GalNAc or Gal residues from blood group AB, A or B erytrocytes.

The active part of the material according to the invention, contains ligand for example at least one Saccharide part which has been bound via a spacer to a Matrix according to:
Saccharide-spacer-Matrix.

Among the functions of the spacer may be mentioned that the spacer separates the Saccharide from the Matrix and binds together the Saccharide with the Matrix.

When the ligand contains or is a polymer, a protein, enzyme or polypeptide, the spacer is not necessary according to the invention and can be chosen to be immobilised to an activated Matrix without spacer.

The immobilization method can be chosen by the expert from several different methods. In many cases an immobilisation method which allows a stable linkage, such as an amide bond or a N-C bond is chosen.

Matrix according to the invention consists for example of a polymer, a plastic, a polysaccharide, or a cross-linked polysaccharide, and can bind several ligand molecules per mL.

The matrix can be magnetic or non-magnetic. If the Matrix is magnetic, this characteristic can be used to separate the matrix from e.g. the whole blood or the plasma using an externally applied magnet during emptying of the whole blood or plasma from the blood bag.

According to the invention Matrix contains at least one of the material agarose 1, 2 or 3.99% or where the agarose percentage value is anywhere between 1 and 3.99% (where percentage denotes the dry weight of agarose in the material per volume swollen agarose (e.g. in water or in buffered water).

Non-limiting example of Matrix is the commercially available Sepharose 2B or Sepharose CL 2B, where CL denotes the cross-linked form.

According to the invention, by using this type agarose, binding of large molecules for example of IgM, which is substantially larger than IgG, can be obtained. This is of importance according to the invention to obtain a higher penetration of this type of large molecules into the pores of Matrix. In previous products especially products in clinical use, such as protein A Sepharose or IgG Sepharose, Sepharose 4B or other material with less porosity has been used.

In one variant of the invention, the product according to the invention is characterised by that the coupling of the ligand to Matrix has been carried out in clean rooms accepted for the clinical use of the product and/or that the product has been sterilised for example by autoclaving or other accepted method for clinical use.

Saccharide symbolizes saccharide which has a biological or other affinity to another molecule, e.g. protein, such as antibody or toxin, virus or cell. Saccharide can consist of a glycoprotein, a neoglycoprotein, a glycopeptide or a glycosylated amino acid, a glycolipid, or a part, a fragment or a modified variant thereof, or another biologically active di- or trisaccharide or higher oligosaccharide substance.

The Saccharide as defined above can be produced chemically or with biological methods, e.g. involving recombinant cells or bacteria, or by a combination of these methods.

The Saccharide may consist of one or more di-, tri, or higher oligosaccharides linked together synthetically, e.g. via an organic molecule, a peptide, e.g. a polypeptide containing one or more lysine residues or containing one or more glutamate residues, or a protein.

A few non-limiting examples of biologically active Saccharide, spacer and Matrix which can be used according to the invention, are given below.

The function of the Saccharide is to bind to one or more the molecules mentioned above. Saccharide may consist of blood group determinants, e.g. blood group A, blood group B, e.g. the A- or B- trisaccharide determinants, or higher oligosaccharide variants thereof containing the A- or B- trisaccharide determinants or containing the GalNAc$\alpha$1-3Gal$\beta$- or Gal$\alpha$1-3 Gal$\beta$-structure, other blood group determinants, carbohydrate structures found on gangliosides, e.g. terminal or internal di-, tri- or higher oligosaccharide structures found in gangliosides of the type GQ1b, GT1a, GD3, GM1 or GM2, e.g. containing the disaccharide structure NeuNAc($\alpha$2-8)NeuNAc($\alpha$2-3), the trisaccharide structure NeuNAc($\alpha$2-8)NeuNAc($\alpha$2-3)Gal, or tetra-, penta- or higher oligosaccharide structures containing one or more of these di- or trisaccharide structures.

In a variant of the invention, the product is further characterised by that it has e.g. been sterilized, e.g. autoclaved, treated with heat and or steam, or treated with other sterilization method such as UV-light or ethylene oxide. The product is further characterized by that it has been optionally produced under validated clean room conditions to allow for function and safety for its clinical use purpose.

The spacer is for example an organic molecule, according to non-limiting examples below of Saccharide-spacer:
Saccharide-O—(CH$_2$)$_m$PhNH—, covalently linked to matrix or to spacer-Matrix Or Saccharide-O—(CH$_2$)$_m$PhNH—C(O)—, covalently linked to matrix or to spacer-Matrix Or
Saccharide-O(CH$_2$)$_n$NH—, covalently linked to matrix or to spacer-Matrix
Or
Saccharide-O(CH$_2$)$_n$NH—C(O)—, covalently linked to matrix or to spacer-Matrix
Or
Saccharide-O(CH$_2$)$_n$NH—(CH$_2$)$_m$PhNH—, covalently linked to matrix or to spacer-Matrix
Or
Saccharide-N(Ac)—(CH$_2$)$_m$PhNH—, covalently linked to matrix or to spacer-Matrix
Or
Saccharide-O(CH$_2$)$_n$NH—(CH$_2$)$_m$PhNH—CO—, covalently linked to matrix or to spacer-Matrix
Or
Saccharide-N(Ac)—(CH$_2$)$_m$PhNH—CO—, covalently linked to matrix or to spacer-Matrix Thus, the Product material may consist of as a non-limiting example:
Saccharide-O(CH$_2$)$_n$NH—(CH$_2$)$_m$PhNH—CO—(CH$_2$)$_m$NH—CH$_2$—CH(OH)—CH$_2$—O-Matrix
Saccharide-N(Ac)—(CH$_2$)$_m$PhNH—CO—(CH$_2$)$_m$NH—CH$_2$—CH(OH)—CH$_2$—O-Matrix
Where in the structures above n and m is an integer=1,2,3 or higher.
Saccharide-O(CH$_2$)$_n$NH—(CH$_2$)$_m$PhNH—, Or
Saccharide-N(Ac)—(CH$_2$)$_m$PhNH—CO—, may also be covalently linked to matrix or to spacer-Matrix via a dimeric or multimeric spacer molecule, e,g, a peptide or a protein.

The Saccharide-Spacer molecules exemplified above may be prepared e.g. by using chemical and/or enzymatic methods and/or using a metabolically engineered cell or recombinant cell containing genes for either of or several of α- or β- fucosyl-, galactosyl-, N-acetyl-galactosaminyl-, N-acetyl-glucosaminyl-transferases or sialyltransferase(s) and genes used for expression of enzymes producing GDP-Fuc, UDP-Gal, UDP-GalNAc, for preparation of the saccharide or for preparation of Saccharide-OR where R is an aliphatic or aromatic compound e.g. Saccharide-O-allyl or Saccharide-O-propargyl, or other Saccharide-O-organic molecule, using eg Lactos-OR for example lactose-allyl or lactose-propargyl glycoside, as the initial acceptor for the reactions with enzymes, glycosyltransferase or for the metabolically engineered cell glycosyltransferases.

The latter compounds produced in this way may according to the invention be reacted with NH2—(CH$_2$)$_m$PhNO2 to give Saccharide-O(CH$_2$)$_n$NH—(CH$_2$)$_m$PhNO2 and this product can then be reduced to Saccharide-O(CH$_2$)$_n$NH—(CH$_2$)$_m$PhNH2, which can be coupled covalently to different compounds or activated matrixes yielding the product material according to the invention.

If not a glycoside is produced by the organic or enzymatic or metabolically engineered cell glycosyltransferases, the produced saccharide may be reacted with NH2—(CH$_2$)$_m$PhNO2 to give Saccharide-NH—(CH$_2$)$_m$PhNHO2 which may be reduced after acetylation to give Saccharide-N(Ac)—(CH$_2$)$_m$PhNH2.

Saccharide above is not limited to any specific saccharide structure but may be for example a blood group A determinant, e.g. blood group determinant A or B, GM1, other sphingolipid carbohydrate structure e.g. of the lacto-, neolacto-, globe- or ganglioserie carbohydrate structure, Lewis blood group determinants, Galα1-3Gal, GalNAcα1-3Gal, GalNAcα1-3Galβ1-3GlcNAc, GalNAcα1-3Galβ1-4Glc-NAc or higher saccharide containing GalNAcα1-3Galβ1-3GlcNAc or GalNAcα1-3Galβ1-4GlcNAc.

The product according the invention may also contain another Matrix e.g. a plastic or a polysaccharide, for example cross-linked agarose, for example of the type Sepharose$^R$ CL-4b or 4Fast Flow, e.g. Sepharose Fast Flow to which with a ligand such as Saccharide-spacer exemplified above has been bound.

In this variant of the invention the part of the product which contains the less porous product for example based on Sepharose 4FF may preferentially bind smaller molecules than for example IgM, for example in blood, such as for example blood group A or B specific IgG molecules and the more porous product according to the invention based on e.g. Sepharose 2 B or a crosslinked variant thereof, is used to complement the binding and removal of for example IgM specific for blood group A and/or blood group B.

The product can be applied for example for reduction and or removal of blood group A and/or B specific antibodies in connection with for example blood donation or after blood donation with the product used in a plasma, bag system.

The invention relates in a specific embodiment to the combined use of the product according to the invention to remove anti-A and anti-B antibodies together with the use of enzymes, such as N-acetyl-α-D-galactosaminidase specifically cleaving GalNAc from blood group A erytrocytes resulting in blood group O erythrocytes, and α-D-galactosidase cleaving galactose (Gal) from blood group B erythrocytes resulting in blood group O erythrocytes.

This embodiment of the invention and treatment results in conversion of AB, A or B blood to whole blood which is universal, lacking blood group determinants A and B on erythrocytes and lacking anti-A and anti-B antibodies.

The product according to the invention can also be used for example in connection with extra-corporal blood or blood plasma treatment of a graft recipient before and/or after transplantation of a blood group incompatible graft such as a donor kidney, liver, heart, lung or bone marrow. In this application the product according to the invention is used in a column connected via for example a plasma centrifuge to the patient, and blood or plasma from the patient is passed through the product and returned to the patient in a continuous manner during the treatment. The treatment can be repeated one or several times.

In still another variant of the method the product may be used to remove anti-A/B antibodies and hydrolyse IgG and/or IgM molecules in an extra-corporal treatment where the patient's blood is passed through the product filled in a column. In this application the product according to the invention contains at least one proteolytic enzyme bound to Matrix for example ides or another proteolytic enzyme specific for cleavage of IgG or another protease for cleavage of IgM. This application is of interest for example in connection with ABO-incompatible transplantation of a sensitized patient.

In the application where IdeS (ides above, Immunoglobulin G degrading enzyme of. *Streptococcus pyogenes*) or another proteolytic enzyme for example EndoS which hydrolysis saccharides from IgG or another enzyme degrading specifically proteins or other molecules in human blood, is used as ligand bound to matrix, the matrix can be based on for example agarose or cross-linked agarose.

IdeS or other enzyme mentioned above, can be covalently bound to the matrix giving a product which can be filled into a column and used for example in the application extra-corporal treatment of human blood or blood plasma. This is described below for IdeS, but the below mentioned description for IdeS as ligand, can also be applied according to the invention for EndoS or other enzyme substituted for IdeS as ligand.

IdeS is covalently bound via reaction between IdeS and activated matrix (for example activated form of agarose or cross-linked agarose for example 2B or 4B or 6B or cross-linked agarose for example Sepharose CL-2B, CL-4B, 4FF or CL-6B).

There can be a spacer molecule between the IdeS molecule and the matrix. Before coupling IdeS to the matrix or to spacer-matrix, matrix or spacer-matrix has been activated with a reactive group which can react with IdeS molecule to give a covalent coupling between IdeS and matrix or spacer-matrix. There are several reactive groups which may be chosen for this purpose as well as methods for activation and coupling to matrix or spacer-matrix. One example is coupling IdeS to N-hydroxysuccinimide (NHS) activated matrix or to NHS-activated spacer-matrix. An example is NHS-activated Sepharose, for example NHS-activated Sepharose CL-4B, CL-6B or 4FF. The linkage is formed between at least one amino group on IdeS and at least one carbonyl group on the activated Sepharose giving an NH—CO linkage. The linkage may then be via a spacer, or between IdeS and the agarose (Sepharose).

The spacer can contain for example a CO—(CH2)nNH— group where n is an integer between 1 and 8. The linkage to matrix can also be for instance IdeS-NH—CO—O-matrix In one preferred embodiment the product contain the following version of IdeS-spacer-Matrix:

IdeS-NH—CO—(CH2)nNH—CH2CH(OH)CH2—O-agarose or

IdeS-NH—CO—(CH2)nNH—CH2CH(OH)CH2—O-cross-linked agarose (e.g. cross-linked agarose 4B, 4FF or CL-6B), obtained by reacting IdeS with NHS-activated spacer-matrix and where NH in IdeS-NH- denotes an amino group in IdeS.

The IdeS can also be bound via other type of linkage (cf. description above or as described below).

There can be single, two or more linkages, or —NH—CO linkages between IdeS and the spacer-matrix.

In another variant for example epoxy-activated agarose, tosyl-activated agarose, or CNBr-activated matrix may be used (in this context matrix is for example cross-linked agarose or Sepharose variants as exemplified above).

The coupling reaction between IdeS and activated matrix or activated spacer-matrix can be carried out at conditions chosen by the expert, for example at a pH value which is any value between 5 to 10 and at a temperature which is any temperature chosen between 2 to 37 degrees Celcius and which a reaction time which is any value between 30 minutes to 30 hours. The exact conditions are chosen by the expert and do not limit the scope of the invention.

The quantity of IdeS per mL of matrix is chosen by the expert for the application. Examples of preferred embodiments are: A quantity of IdeS between 10 mikrogram and 100 mikrogram per mL, between 100 mikrogram and 1 mg per mL and between 1 and 10 mg per mL of matrix or spacer-matrix.

The IdeS-matrix or IdeS-spacer-matrix is further characterized by that in a preferred embodiment the product is produced in clean areas/vessels according to GMP-requirements under controlled bioburden and endotoxin conditions and under a validated quality system to allow clinical application.

In one preferred embodiment the IdeS-matrix or IdeS-spacer-matrix (hare called IdeS-matrix) is filled in columns and columns are sealed and sterilized if required. The method of filling IdeS-matrix consist of that for example the IdeS-matrix is filled through a side-hole in the column or for example into the cylinder, and after filling is sealed with a side-hole plug or with a lock. The product is thereafter sterilized conventionally and if used clinically with a validated method.

The column may for example have an inner volume (volume of IdeS-matrix filled inside the column) which is one volume of the volumes between 1 mL to 0.5 L. In a preferred embodiment the column have an inner volume of IdeS-matrix with a value between 50 to 100 mL or 60, 62, 64 mL of IdeS-matrix or a volume between these values. The column contains for example the following: One cylinder with or without a side-hole for filling of IdeS-matrix, one or two circular locks, for example one lock connected at the top of the cylinder and one lock connected at the bottom of the cylinder, one or two nets which are situated between the lock and the cylinder and the IdeS-matrix. Each lock or one of the locks may be provided with a circular opening with a hollow protruding part in the center of the lock for connection of a tubing for inflow and outflow of blood of blood plasma. A tubing is connected to each hole on each lock via a protruding circular plastic part on each lock. The tubings are connected to the in and outflow respectively of blood or blood plasma to and from the column.

As a preferred example of a configuration of the column, the each circular net is first mounted in ring made of silicon which is placed between each lock and cylinder. The bottom and top net with silicon ring are locked between one bottom lock one cylinder and one top lock by pressing together the locks and the cylinder. In one preferred embodiment of this variant, each lock is provided with one, two or up to 20 separate protruding clips on the outer edge of the circular lower outer surface of the lock, said clips having the ability to be secured under an edge running around the top and bottom, respectively, of the cylinder via a click mechanism when the lock and the cylinder are presses together.

The net may have holes to allow passage of blood or plasma with a diameter of any value in the range between 20 and 150 mikrometer and in preferred embodiments for example having a value between 20 and 40 mikrometer.

The matrix may consist of particles with a diameter in the range between 20 and 200 mikrometer and in preferred embodiments having a value between 50 and 100 mikrometer. The column contains an inlet and an outlet for inflow and outflow respectively of blood or blood plasma to allow passage of plasma through IdeS-matrix. The inlet and outlet may be via the top- and bottom-locks respectively, the inlet and the outlet are connected via a tubing and for example luer male and female connectors to a plasma separator or equipment for extra-corporal treatment of blood or blood plasma. The column further contains at least one permeable net or membrane which allows passage of blood or blood plasma through the net, but the net or membrane does not allow passage of IdeS-matrix. The column can be connected to a machine for example a machine for blood plasma separation such as a centrifuge or a blood plasma filter. The machine is connected to a blood line from the patient and blood is for example separated with the blood plasma separator and the plasma line is passed through the product according to the invention and the outlet from the product is connected to the blood line back to the patient to allow a continuous extra-corporal treatment of the blood in the patient. The IdeS in the column specifically cleaves the IgG molecules in the human blood or plasma upon passage of the human blood or plasma through the column.

The flow rate is determined by the expert and is chosen to be for example up to 50 mL per minute or higher depending on the flow properties of the column and the proteolytic on IgG of the IdeS.

In another example, the product can be applied for extra corporal reduction or removal of IgM molecules for example for patients with certain autoimmune disorders, where ligand specific for IgM molecules is bound to Matrix as described above and product used filled in a column as above.

The invention claimed is:

1. A combined product for selective binding and cleavage of biomolecules in human blood or plasma comprising: (a) column and a matrix, said matrix being filled into said column, wherein at least one blood group A saccharide with specificity to bind to anti-A antibodies and/or at least one blood group B saccharide with specificity to bind to anti-B antibodies are bound to the matrix, optionally via a spacer, and (b) wherein said matrix further comprises at least one hydrolytic enzyme with specificity to cleave a blood group A saccharide, a blood group B saccharide, or combinations thereof.

2. The combined product according to claim 1, wherein the enzyme is N-acetyl-alpha-D-galactosaminidase specifically cleaving GalNAc from blood group A erythrocytes and/or alpha-D-galactosidase specifically cleaving galactose from blood group B erythrocytes.

3. The combined product of claim 2, wherein the enzyme is N-acetyl-alpha-D-galactosaminidase specifically cleaving GalNAc from blood group A erythrocytes.

4. The combined product of claim 2, wherein the enzyme is alpha-D-galactosidase specifically cleaving galactose from blood group B erythrocytes.

5. The combined product according to claim 1, wherein the matrix is agarose.

6. The combined product according to claim 5, wherein the matrix is cross-linked agarose.

7. The combined product according to claim 5, wherein the matrix is NHS-activated Sepharose selected from the group consisting of NHS-activated Sepharose CL 4B, CL-6B, and 4FF.

8. The combined product according to claim 1, wherein the spacer contains a —CO—(CH2)nNH-group, wherein n is an integer of 1-8.

9. The combined product according to claim 1, wherein in the case when there is no spacer, said at least one blood group A saccharide and/or said at least one blood group B saccharide are covalently bound to the matrix.

10. The combined product according to claim 1, wherein the column filled with said at least one blood group A saccharide and/or said at least one blood group B saccharide bound to the matrix, optionally via a spacer, is provided with one inlet and one outlet for inflow and outflow of human blood or plasma.

11. The combined product of claim 1, wherein the blood group saccharide A is present on red blood cells of blood group A and the blood group saccharide B is present on red blood cells of blood group B.

12. The combined product of claim 1, wherein the combined product is suitable for converting the blood group A saccharide and/or the blood group B saccharide to a blood group O saccharide.

13. The combined product of claim 1, wherein at least one Hood group A saccharide with specificity to bind to anti-A antibodies is bound to the matrix, optionally via a spacer.

14. The combined product of claim 1, wherein at least one blood group B saccharide with specificity to bind to anti-B antibodies is bound to the matrix, optionally via a spacer.

15. The combined product of claim 1, wherein at least one blood group A saccharide with specificity to bind to anti-A antibodies and at least one blood group B saccharide with specificity to bind to anti-B antibodies are bound to the matrix, optionally via a spacer.

16. The combined product of claim 1, wherein the blood group A saccharide and the blood group B saccharide are chosen from blood group A- or B- trisaccharide determinants or higher oligosaccharides variants thereof containing A- or B- trisaccharide determinants or containing a GalNAc$\alpha$1-3Gal$\beta$- or Gal$\alpha$1-3 Gal$\beta$ structure.

17. A method for treating donated blood of blood group A, B, or AB, comprising:
passing the donated blood through the combined product of claim 1, and
obtaining a blood product comprising blood group O red blood cells,
wherein the blood product has decreased levels of anti-A antibodies and/or anti-B antibodies when compared to levels of anti-A antibodies and/or anti-B antibodies prior to passing through the combined product.

18. A method for extracorporeal treatment of human blood or plasma, comprising:
passing the human blood or plasma through the combined product of claim 1, and
obtaining a blood product comprising treated human blood or plasma.

19. A method for blood transfusion in a patient in need thereof, comprising:
passing untreated blood or plasma through the combined product of claim 1 to form treated blood or plasma, and
transfusing the treated blood or plasma into the patient.

20. A method for extracorporeal removal of anti-A and anti-B antibodies and/or for cleavage of blood group A saccharides and/or blood group B saccharides in human blood or plasma in connection with blood donation or with ABO-incompatible transplantation of a sensitized patient, wherein the blood or plasma of the patient is passed through the combined product as defined in claim 1.

* * * * *